US005562402A

United States Patent [19]
Muto

[11] Patent Number: 5,562,402
[45] Date of Patent: Oct. 8, 1996

[54] APPARATUS FOR AUTOMATICALLY DELIVERING GLASS SHEETS FOR PREPARED SLIDES

[75] Inventor: Yunosuke Muto, Tokyo, Japan

[73] Assignee: Muto Pure Chemicals Company, Ltd., Tokyo, Japan

[21] Appl. No.: 450,709

[22] Filed: May 25, 1995

[30] Foreign Application Priority Data

Jun. 1, 1994 [JP] Japan .................................. 6-120072

[51] Int. Cl.$^6$ ............................................... B65G 59/06
[52] U.S. Cl. ...................... 414/797.7; 221/259; 221/277; 414/797.9
[58] Field of Search ............................ 221/203, 259, 221/277; 271/35, 110, 119, 138; 414/797.6, 797.7, 797.9

[56] References Cited

U.S. PATENT DOCUMENTS

| | | | |
|---|---|---|---|
| 2,185,675 | 1/1940 | Mitchell et al. | 271/35 X |
| 3,506,258 | 4/1970 | Lindquist | 271/119 |
| 3,672,771 | 6/1972 | Lakin | 271/35 X |
| 5,050,852 | 9/1991 | Sawada et al. | 414/797.9 X |
| 5,238,143 | 8/1993 | Crighton | 221/7 |
| 5,383,569 | 1/1995 | Muto | 271/110 X |

FOREIGN PATENT DOCUMENTS

| | | |
|---|---|---|
| 0570004 | 11/1993 | European Pat. Off. . |
| 5-61143 | 8/1993 | Japan . |
| 6-20348 | 3/1994 | Japan . |
| 1466561 | 3/1977 | United Kingdom . |
| 2258459 | 2/1993 | United Kingdom . |

*Primary Examiner*—Karen Merritt
*Assistant Examiner*—Janice L. Krizek
*Attorney, Agent, or Firm*—Fish & Richardson P.C.

[57] ABSTRACT

An apparatus is provided for automatically delivering a glass sheet for a preparation. The apparatus including a rack for receiving a stack of glass sheets, rollers for feeding out a lowest glass sheet until the lowest glass sheet has been completely ejected from the stack, and a switch mechanism capable of terminating the operation of the rollers by the contact of the leading edge of the lowest glass sheet. The roller includes a plurality of protrusions for pushing the trailing edge of the lowest glass sheet in order to operate the switch mechanism by the contact of the leading edge when the lowest glass sheet has been completely ejected from the stack. The switch mechanism can reliably be operated by the force of the pushing operation.

12 Claims, 11 Drawing Sheets

APPARATUS FOR AUTOMATICALLY DELIVERING GLASS SHEETS FOR PREPARED SLIDES

BACKGROUND OF THE INVENTION (i) Field of the Invention

The present invention relates to an apparatus for automatically delivering glass sheets for prepared slides one by one.

(ii) Description of the Related Art

FIG. 9 shows an apparatus for automatically delivering glass sheets for prepared slides suggested by the present applicant in Japanese Utility Model Laid-open Publication No. 5-61143(JU-A-05-61143).

In FIG. 9, a rack 10 for receiving a plurality of laminated glass sheets for thin type prepared slides (hereinafter merely referred to as "glass sheets") is mounted on a body 8, and glass sheets 12 at the lowest stage are successively delivered by the body 8. More specifically, when the rack 10 is set onto the mounting surface of the body 8, the upper portion of a roller 15 protrudes into an opening 10A formed in the lower surface plate of the rack 10, and as a result, the lowest glass sheet 12 is pushed up. In this state, the roller 15 is rotated, whereby the glass sheet 12 is forwardly fed through an ejection opening 14. In this state, the glass sheet 12 is also forwardly urged against the rack 10 itself, but the movement of the glass sheet 12 is restrained by means of a stopper 9. The reason why the glass sheets are obliquely maintained is that the contact pressure of the roller 15 is increased so as to readily eject the lowest glass sheet through the ejection opening 14.

When the glass sheet 12 is fed into a passage 16, its leading edge pushes down (or pushes up) a plate spring type switch 18 which extends into the passage 16, with the result that a motor 20 stops and the rotation of the roller 15 stops. When the delivered glass sheet 12 is manually pulled out, the switch 18 returns to its original state, so that the next lowest glass sheet 12 is automatically delivered.

FIGS. 10 and 11 show an apparatus for automatically delivering glass sheets for prepared slides suggested by the present applicant in Japanese Utility Model Laid-open Publication No. 6-20348(JU-A-06-20348). In the apparatus shown in FIG. 9, when the lowest glass sheet is separated from the remaining sheets, sliding resistance between the glass surfaces is so large that the smooth separation is difficult. The apparatus shown in FIGS. 10 and 11 intends to overcome this problem and is characterized in that the glass sheets are vibrated to momentarily reduce load, thereby relieving the sliding resistance between the glass sheets.

In FIG. 10, the lower surface plate of the rack 10 is formed with two openings 10A and 10B, and a rectangular roller 22 and a circular roller 24 protrude into the respective openings and come in contact with the lower surface of the lowest glass sheet 12. In this state, when the two rollers 22 and 24 are rotated, the glass sheet 12 is forwardly fed out. At that time, since the roller 22 is not circular, the rear portion of the glass sheet 12 is moved up and down, whereby the separation of the glass sheet 12 can be facilitated.

In the apparatus shown in FIG. 11, a belt 26 is passed over two rollers 28 and 30, and the belt 26 is provided on the belt surface thereof with a protrusion 31. While vibration is imparted to the glass sheet 12 with the aid of the protrusion 31, the lower surface of the glass sheet is rubbed and fed. It can be contrived that the protruding length of the protrusion 31 is adjusted to the thickness of the glass sheet and the side of the protrusion 31 is hooked on the trailing edge of the lowest glass sheet to push the glass sheet from the rear edge. However, it is difficult to hook the single thin glass sheet alone from the remaining glass sheets.

In the above-mentioned conventional apparatuses, there is a problem that in the stopped state after the lowest glass sheet has been fed out, the next lowest glass sheet partially receives the load of the remaining glass sheets, so that a large force is required to pull out the lowest glass sheet and the removal of the glass sheet cannot be smoothly accomplished.

In the apparatus shown in FIG. 9, at a time when the trailing edge of the glass sheet 12 has passed the apex of the roller 15, the delivery of the glass sheet stops, with the result that the glass sheet 12 also stops (see FIG. 9). However, about a half of the upper surface of the glass sheet 12 is laid under the remaining glass sheets. That is to say, in a range 100 of from A to B in FIG. 9, the load and the sliding resistance are applied to the glass sheet 12, so that it is difficult to manually pull out the glass sheet 12.

This fact is similarly observed in the apparatuses shown in FIGS. 10 and 11. The range of from A to B in FIG. 10 and the range of from A to B in FIG. 11 are laid under the remaining glass sheets, and so resistance to the pulling-out of the glass sheet 12 is generated. Since the glass sheets for the prepared slides are extremely thin, an excessive force cannot be applied thereto, when both the sides of each glass sheet are held to take out the same. Thus, an apparatus capable of taking out the glass sheet by merely lightly holding it has been desired.

On the other hand, in the above-mentioned apparatuses, a mechanism for pushing down the plate spring type switch 18 by the leading edge of the glass sheet 12 is employed, and therefore in order to securely push down the switch, a predetermined delivering force or more is necessary.

However, in the above-mentioned apparatuses, frictional force on the surface of the roller or the upper surface of the protrusion is utilized to deliver the glass sheet. Therefore, in the case that the returning force of the switch is large, there is a problem that the switch cannot be securely operated. If the trailing edge of the glass sheet is pushed from its rear, the delivering force can be directly transmitted to the glass sheet, but it is difficult to hook the trailing edge alone of the lowest glass sheet in the state where the glass sheets are laminated, as described above.

SUMMARY OF THE INVENTION

The present invention has been accomplished in view of the above-mentioned conventional problems. An object of the present invention is to provide an apparatus for automatically delivering a glass sheet for a preparation in which the glass sheet can simply and easily be pulled out.

Another object of the present invention is to provide an apparatus for automatically delivering a glass sheet for a preparation which can securely push down a plate spring type switch for automatic delivery stop.

In order to achieve the aforesaid objects, the present invention has the following characteristics. The first aspect of the present invention provides an apparatus for automatically delivering a glass sheet for a preparation. The apparatus comprises a rack for receiving a stack of glass sheets and a body for supporting the rack and successively delivering the lowest glass sheet. The body comprises feed means for feeding out the lowest glass sheet until the lowest glass sheet has been completely ejected from the rack; and push means for pushing the trailing edge of the ejected glass sheet in order to cause the leading edge of the ejected sheets to push down a delivery stop switch.

The second aspect of the present invention provides an apparatus for automatically delivering glass sheet for a preparation. The apparatus comprises a rack for receiving a stack of glass sheets and a body for supporting the rack and successively delivering the lowest glass sheet. The rack has an ejection opening which is formed in the lower end of a rack front surface plate to eject the lowest glass sheet individually, a rear opening formed in a rack bottom surface plate, and a front end opening formed in the rack bottom surface plate. The body has a rear roller which protrudes into the rear opening and comes in contact with the lower surface of the lowest glass sheet to feed it out, and a front roller which has at least one protrusion on a roller surface and protrudes into the front end opening; the protrusion of the roller coming into contact with the lower surface of the lowest glass sheet to feed it out and pushing the trailing edge of the ejected glass sheet in order to cause the leading edge of the glass sheet ejected through the ejection opening to push down a delivery stop switch.

The third aspect of the present invention provides an apparatus for automatically delivering a glass sheet for a preparation. The apparatus comprises a rack for receiving a stack of glass sheets and a body for supporting the rack and successively delivering the lowest glass sheet. The rack has an ejection opening which is formed in the lower end of a rack front surface plate to eject the lowest glass sheet individually, and an opening formed over the range of from the rear portion to the front end of a rack bottom surface plate. The body has a belt mechanism which has at least one protrusion on a belt surface and protrudes into the opening to contact the lower surface of the lowest glass sheet, thereby feeding it out. The protrusion of the belt mechanism comes into contact with the lower surface of the lowest glass sheet to feed it out and push the trailing edge of the ejected glass sheet in order to cause the leading edge of the glass sheet ejected through the ejected opening to push down a delivery stop switch.

According to the structure of the first aspect of the present invention, the feed means is started to feed out the lowest glass sheet in the state where the rack is mounted on the body. This feed means performs a feeding operation until the lowest glass sheet has been completely ejected and released out of the rack. Thus, no part of the surface of the lowest glass sheet is laid under the remaining glass sheets, and a sliding resistance between the glass sheets is no longer produced.

When the glass sheet is ejected from the rack, the trailing edge of the glass sheet is singly exposed, so that the trailing edge can be readily pushed by the pushing means. The delivery stop switch is then pushed down by the leading edge of the glass sheet, with the result that the operation of the feed means is consequently stopped. The pushing means does not make use of rubbing feed with the aid of frictional force caused by the contact with the glass sheet surface but directly pushes out the trailing edge of the glass sheet, whereby sufficient pushing force can be applied to the glass sheet.

According to the structure of the second aspect of the present invention, when the rack is mounted on the body, the rear roller protrudes into the rear opening of the rack bottom surface plate, while the front roller protrudes into the front end opening. When the rear portion of the stack is pushed up by the rear roller and the rear roller is rotated, the lowest glass sheet is forwardly fed out.

The front roller having the protrusion makes use of the frictional force on the upper surface of the protrusion to effect the forward feeding of the glass sheet and intermittently pushes up the glass sheet by the rotation of the protrusion. Furthermore, after the glass sheet has been ejected through the ejection opening, the trailing edge of the glass sheet is pushed by the side of the protrusion. That is to say, the front roller with the protrusion functions as feed means for feeding out the glass sheet until the lowest glass sheet has been completely ejected and released out of the rack, as vibrating means for facilitating the separation of the lowest glass sheet from the stack of glass sheets, and as pushing means for pushing the trailing edge of the ejected glass sheet to securely push down the delivery stop switch by the leading edge of the glass sheet.

Therefore, according to the structure of the second aspect of the present invention, the lowest glass sheet can be completely released from the rack to simplify the removal of the glass sheet, and the delivery stop switch can be securely started.

According to the structure of the third aspect of the present invention, when the rack is mounted on the body, the belt mechanism protrudes into the opening of the rack bottom surface plate. That is to say, the belt comes in contact with the lower surface of the lowest glass sheet, and by the rotation of the belt itself and the movement of the protrusion caused thereby, the lowest glass sheet can be fed out. Simultaneously, vertical vibration is intermittently applied to the remaining glass sheets by virtue of the movement of the protrusion. Thus, the lowest glass sheet is completely ejected out of the ejection opening and released from the rack, and the trailing edge of the glass sheet is then pushed by the side of the protrusion. That is to say, similarly to the above, the belt with the protrusion has the function of feed means for feeding out the glass sheet until the lowest glass sheet has been completely ejected and released out of the rack, of vibrating means for facilitating the separation of the lowest glass sheet from the other glass sheets, and of pushing means for pushing the trailing edge of the ejected glass sheet to securely push down the delivery stop switch by the leading edge of the glass sheet.

Therefore, according to the structure of the third aspect of the present invention, the lowest glass sheet can be released from the rack to simplify the pulling-out of the glass sheet, and the delivery stop switch can be securely activated.

DETAILED DESCRIPTION OF THE INVENTION

The present invention will be described on the basis of suitable embodiments with reference to attached drawings.

Figure 1:
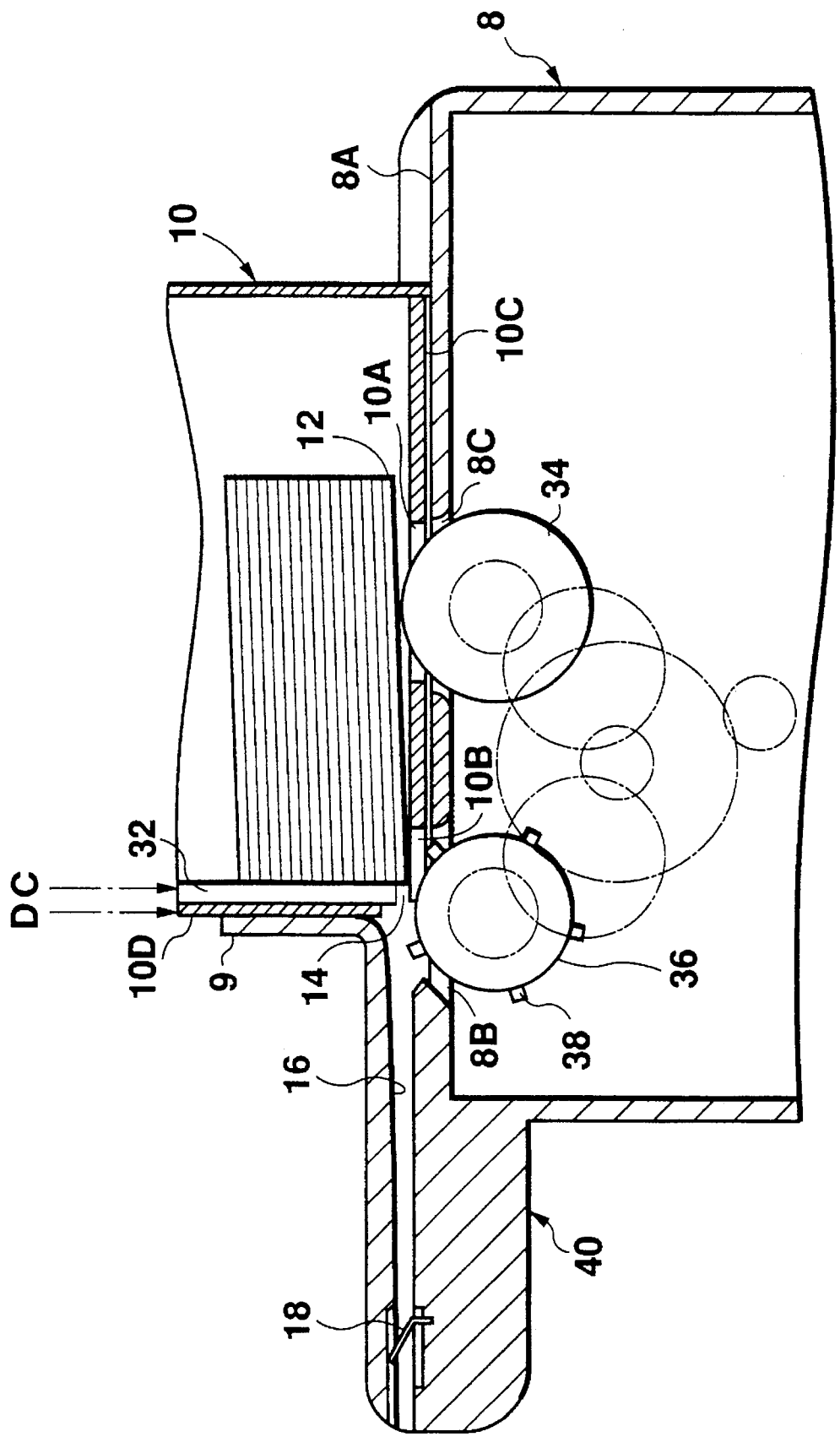
FIG. 1 is a sectional view illustrating a first embodiment of an apparatus for automatically delivering a glass sheet for a preparation according to the present invention.
Figure 2:
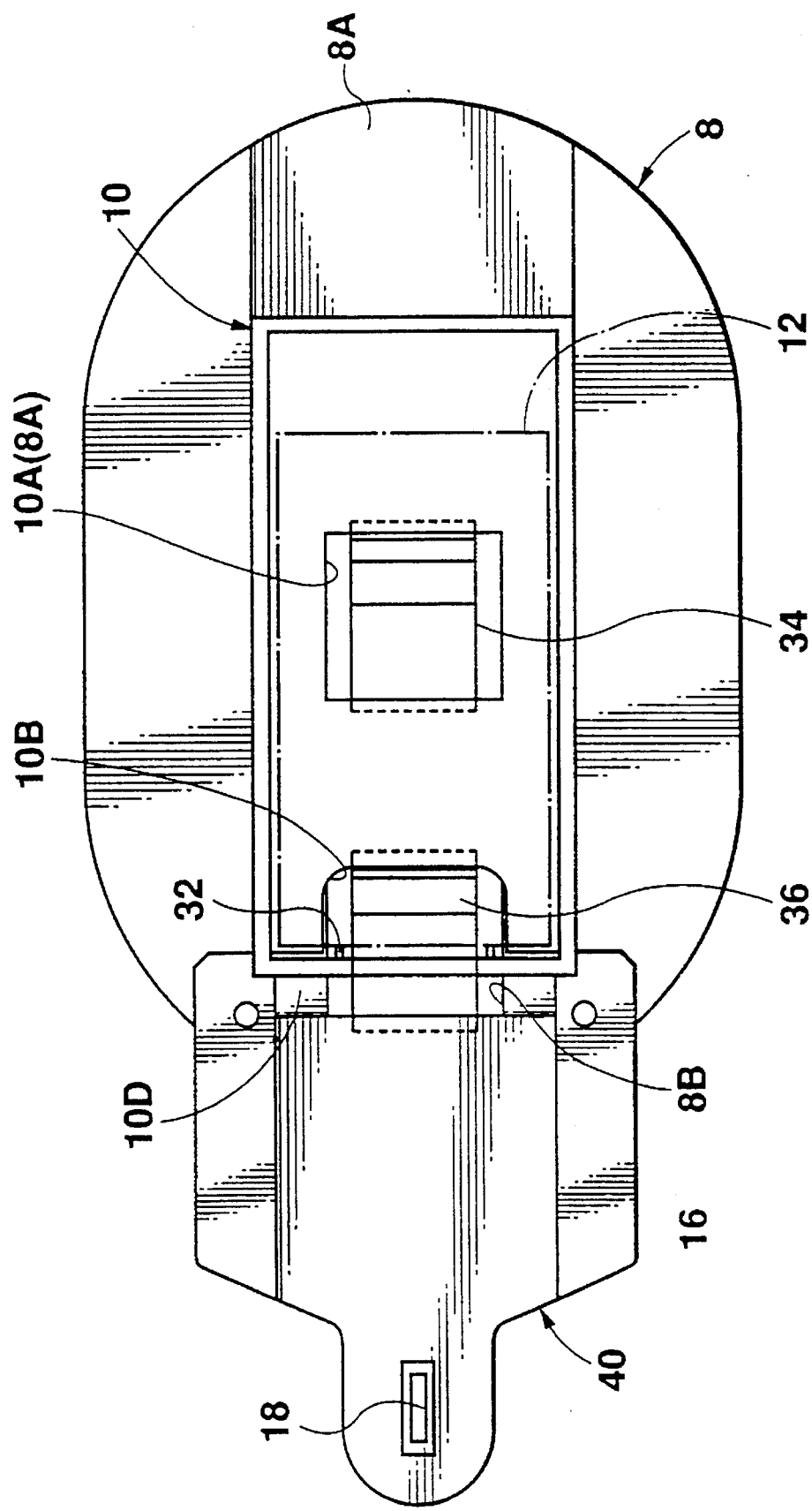
FIG. 2 is a top view of the apparatus shown in FIG. 1

In FIG. 1, an apparatus for automatically delivering a glass sheet for a preparation according to the present invention is shown. FIG. 1 is the sectional view of the apparatus. FIG. 2 shows a top view of the apparatus in which a glass sheet passage 16 is exposed.

In FIGS. 1 and 2, a rack 10 receiving a stack of glass sheets is mounted on a mounting surface 8A formed on a body 8, while the rack 10 is positioned by a stopper 9. The rack 10 has partitions by which the stack having various sizes can be received, but these partitions are not shown in any of the drawings.

The rack 10 is provided at the lower end of a front plate 10D thereof with an ejection opening 14. Actually, the size of the ejection opening 14 is decided by the level of the lower ends of aperture setting bars 32 with respect to a bottom surface plate 10C. The two aperture setting bars 32 are provided inside the front surface plate 10D as shown in FIG. 2. In the present embodiment, the center (a position C in FIG. 1) of the aperture setting bar 32 coincides with the position of the leading edge of the bottom surface plate 10C.

At a position slightly behind the central portion of the bottom surface plate 10C, an opening 10A is formed in the bottom surface plate 10C, and also at the front end of the bottom surface plate 10C, an opening 10B is formed.

The body 8 has a rear roller 34 having an exposed upper portion and a front roller 36. The mounting surface 8A is provided with an opening 8C corresponding to the opening 10A of the rack 10, and the upper portion of the rear roller 34 upwardly enters the opening 8C and further protrudes into the opening 10A to push up a slightly rearward part of the lower surface of the lowest glass sheet 12.

The mounting surface 8A is provided with an opening 8B corresponding to the opening 10B of the rack 10, and the upper portion of the front roller 36 upwardly protrudes into the opening 8B and further protrudes into the opening 10B.

In the present embodiment, the axis of the front roller 36 is set at a position D in front of a position C of the ejection opening 14. A roller surface is provided with five protrusions 38, and in the present embodiment, the diameter of the front roller 36 including the protrusions 38 is the same as that of the rear roller 34. The rear roller 34 and the front roller 36 are rotated together by a drive mechanism. This drive mechanism is driven by a motor not shown.

The front roller with the protrusions has three important functions. The first function is a feeding function for feeding out the lowest glass sheet until it has been completely ejected and released from the ejection opening 14 of the rack 10, whereby the upper surfaces of the protrusion 38 successively come in contact with the lower surface of the lowest glass sheet 12 and deliver the glass sheet 12 by rubbing friction. The second function is a vibrating function for facilitating the separation of the glass sheet 12, whereby when the front roller rotates, the protrusions intermittently push up the lower surface of the glass sheet 12. The third function is a pushing function for pushing the trailing edge of the ejected glass sheet 12 by the side of the protrusion 38 to securely cause the leading edge of the glass sheet 12 to push down the delivery stop switch 18.

Figure 12:
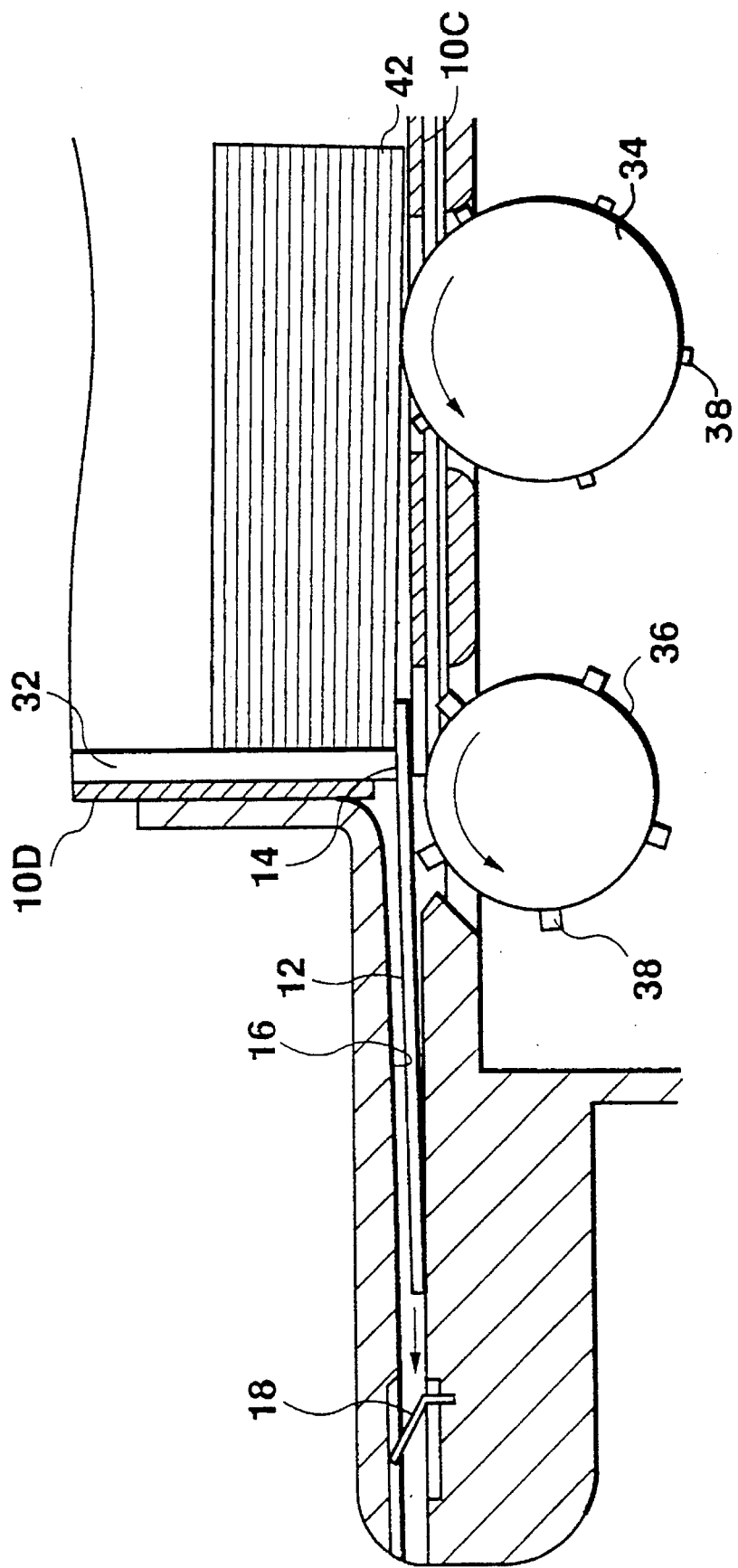
FIG. 12 is a sectional view illustrating a third embodiment of the apparatus for automatically delivering a glass sheet for a preparation according to the present invention.

If a roller having a plurality of protrusions 38 (which is the same as the front roller) is used as the rear roller 34, as shown in FIG. 12, the feeding force can be increased and the vibrating function can also be increased. In addition, as the rear roller, a polygonal roller can also be used.

When the ejected glass sheet 12 moves forward along the passage 16 and its leading edge pushes down the plate spring type switch 18, the motor connected to the switch 18 stops.

Next, the operation of the apparatus according to the present embodiment will be described with reference to FIGS. 1, and 3 to 7.

Figure 3:
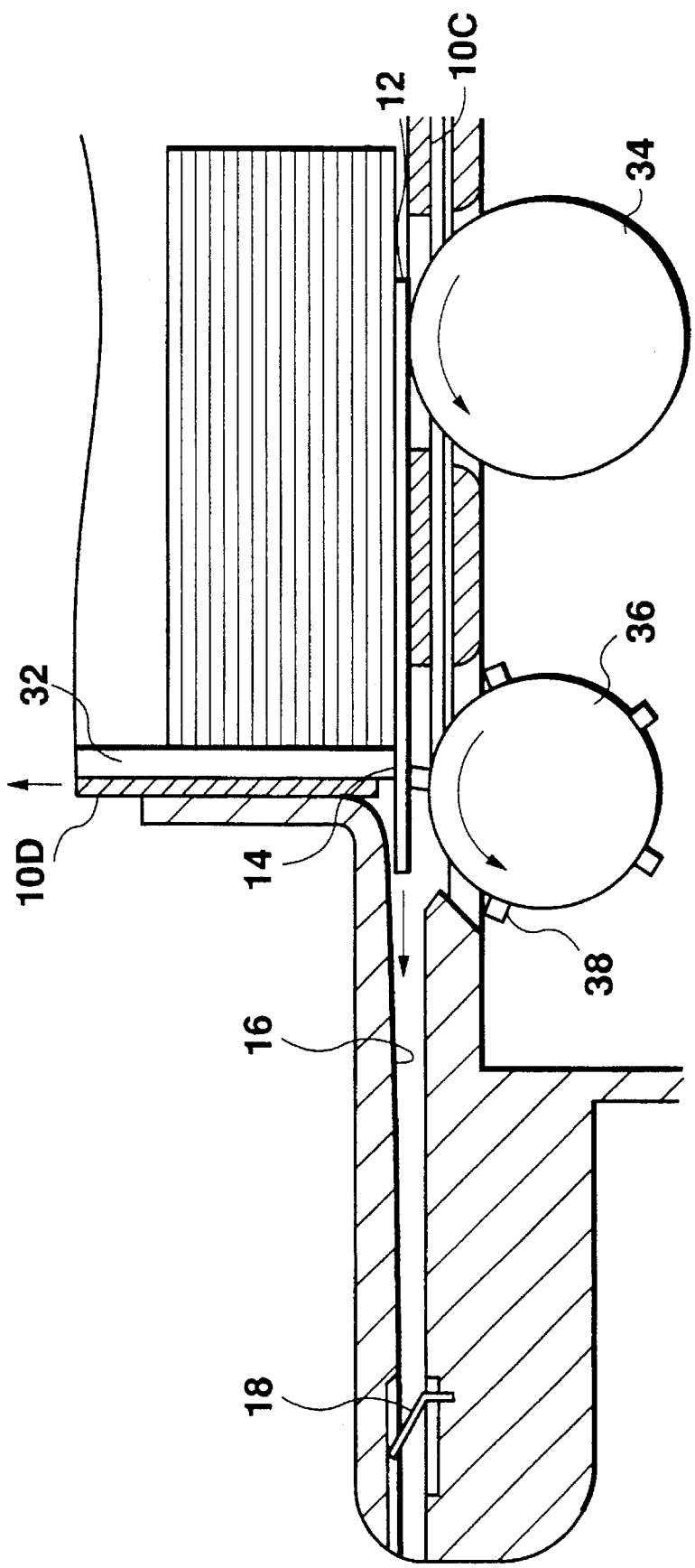
FIG. 3 shows the operation of the first embodiment.

In a rack setting state shown in FIG. 1, when the switch (not shown) of the motor is turned on, the drive mechanism starts, so that the rear roller 34 and the front roller 35 rotate at the same rotational speed. At this time, as shown in FIG. 3, the lowest glass sheet 12 is forwardly fed out by the frictional force of the rear roller 34. In consequence, the protrusion 38 moved to the upper portion of the front roller 36 comes in contact with the lower surface of the glass sheet 12 to produce frictional force, whereby the front roller 36 cooperates with the rear roller 34 to feed out the glass sheet 12 forward. At the same time, the glass sheet 12 is upwardly pushed by the protrusion 38, and the rack 10 itself is also pushed upward by means of the glass sheet 12. Then, the plurality of protrusions successively push up the lower surface of the glass sheet 12, whereby the whole rack 10 vibrates. This vibration reduces contact resistance between the remaining glass sheets, so that the glass sheet can be easily ejected.

Figure 4:
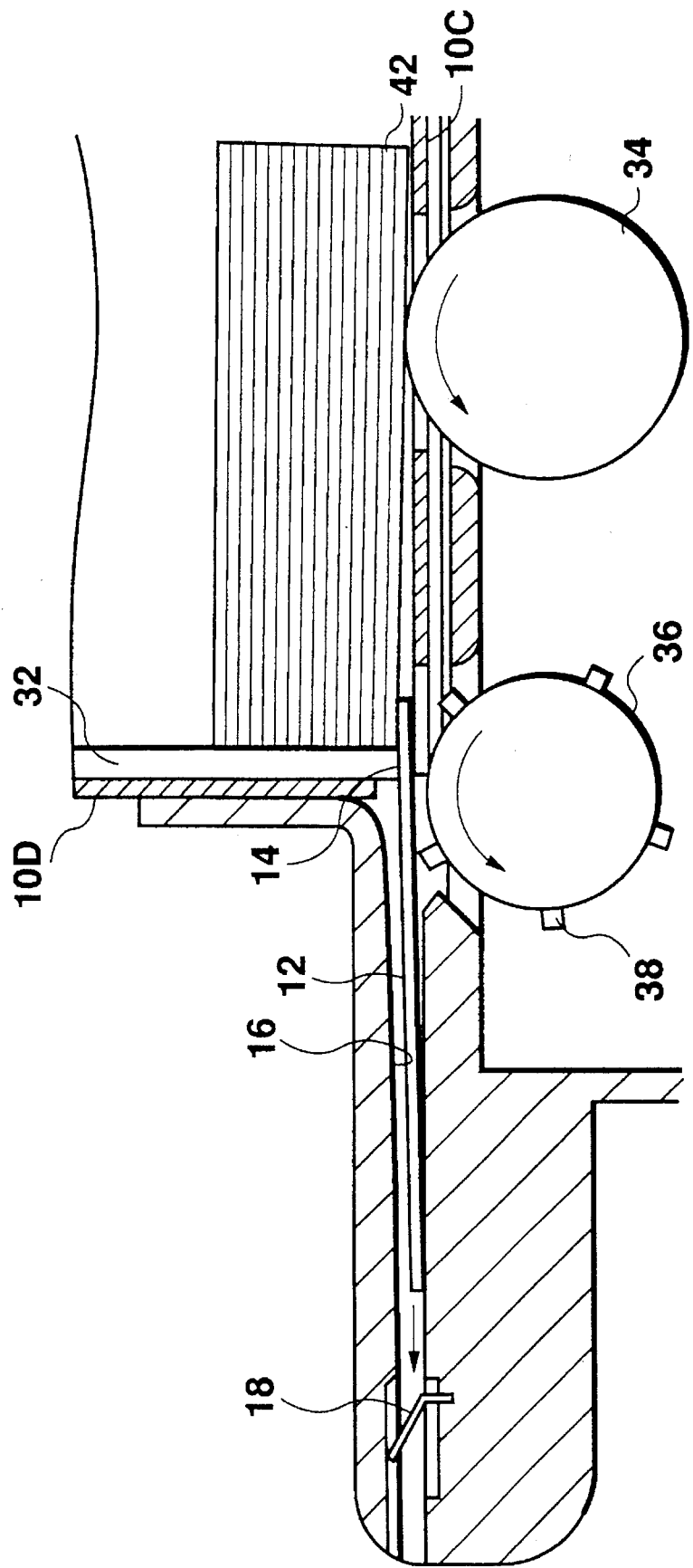
FIG. 4 shows the operation of the first embodiment.

As shown in FIG. 4, when the glass sheet 12 moves forward, it is released from the contact with the rear roller 34, but even in this state, the contact state of the glass sheet 12 with the front roller 36 is securely maintained, so that the glass sheet 12 is forward fed out as it is. Here, since the axial center D of the front roller 36 is set in front of the center position C of the aperture setting bars 32 which substantially defines the ejection opening 14 as shown in FIG. 1, the feeding function of the front roller 36 can be continuously imparted to the glass sheet 12, until the glass sheet 12 has been completely ejected out of the ejection opening 14. That is to say, the front roller 36 should be positioned so that its apex may be positioned substantially just under or in front of the ejection opening 14.

Figure 5:
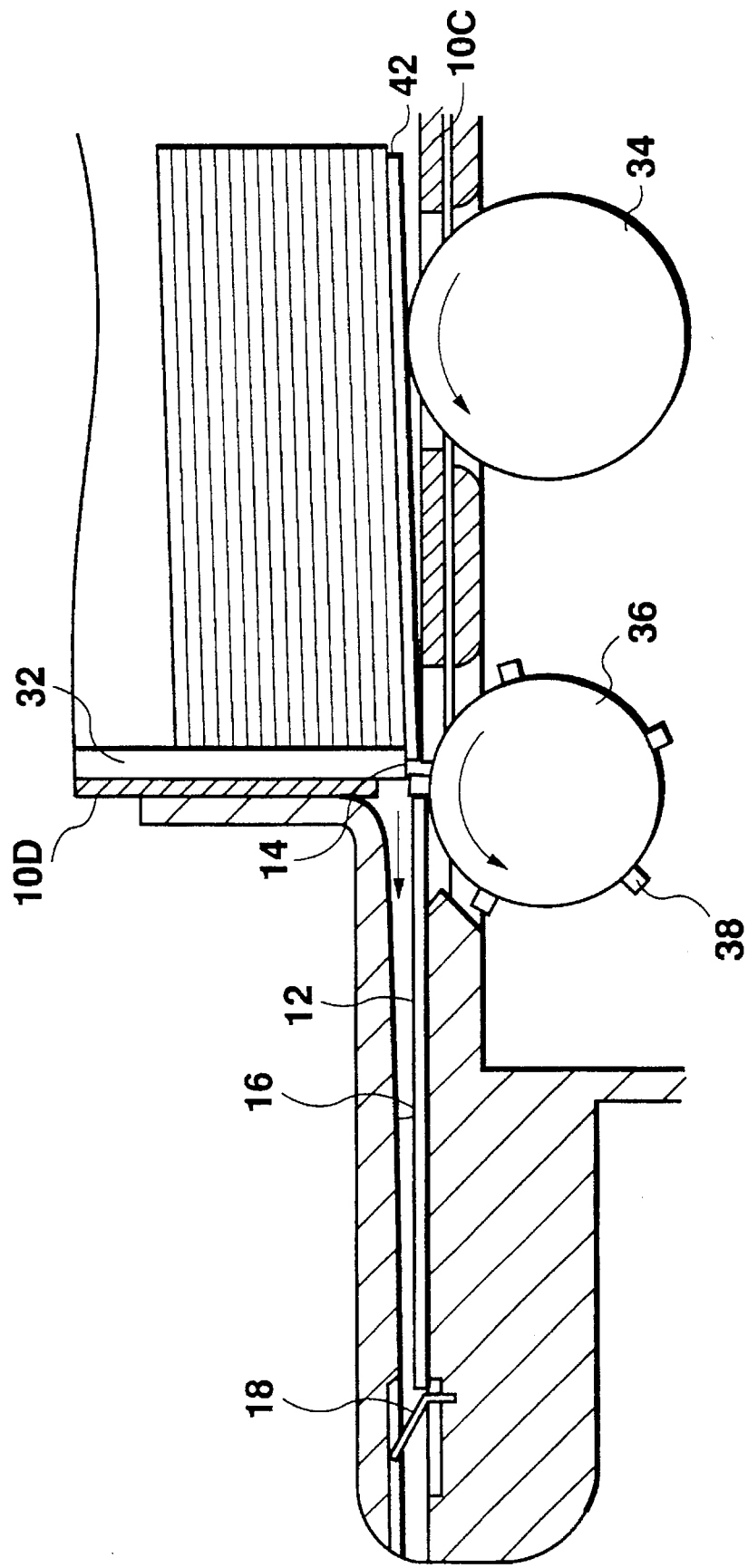
FIG. 5 shows the operation of the first embodiment.

FIG. 5 shows a state where the glass sheet 12 is completely ejected out of the ejection opening 14. In this state, no part of the glass sheet 12 is laid under the remaining glass sheets. Furthermore, since the trailing edge of the glass sheet 12 is singly exposed, it is possible to push the trailing edge. In the state shown in the FIG. 5, the feeding of the next glass sheet 42 is started.

In the present embodiment, in a state where the glass sheet 12 is fed to the passage 16, the whole glass sheet 12 falls in front of the protrusion 38, as shown in FIG. 5. Therefore, when the front roller 36 is rotated, the side of the protrusion positioned on an upper side naturally hits against the trailing edge of the glass sheet 12 to push the glass sheet 12. A stroke distance of the glass sheet which can be pushed by the side of the protrusion is decided by a relationship between the thickness of the glass sheet present on the passage 16 and the orbit of the protrusion, and it depends upon the diameter of the front roller 36.

Figure 6:
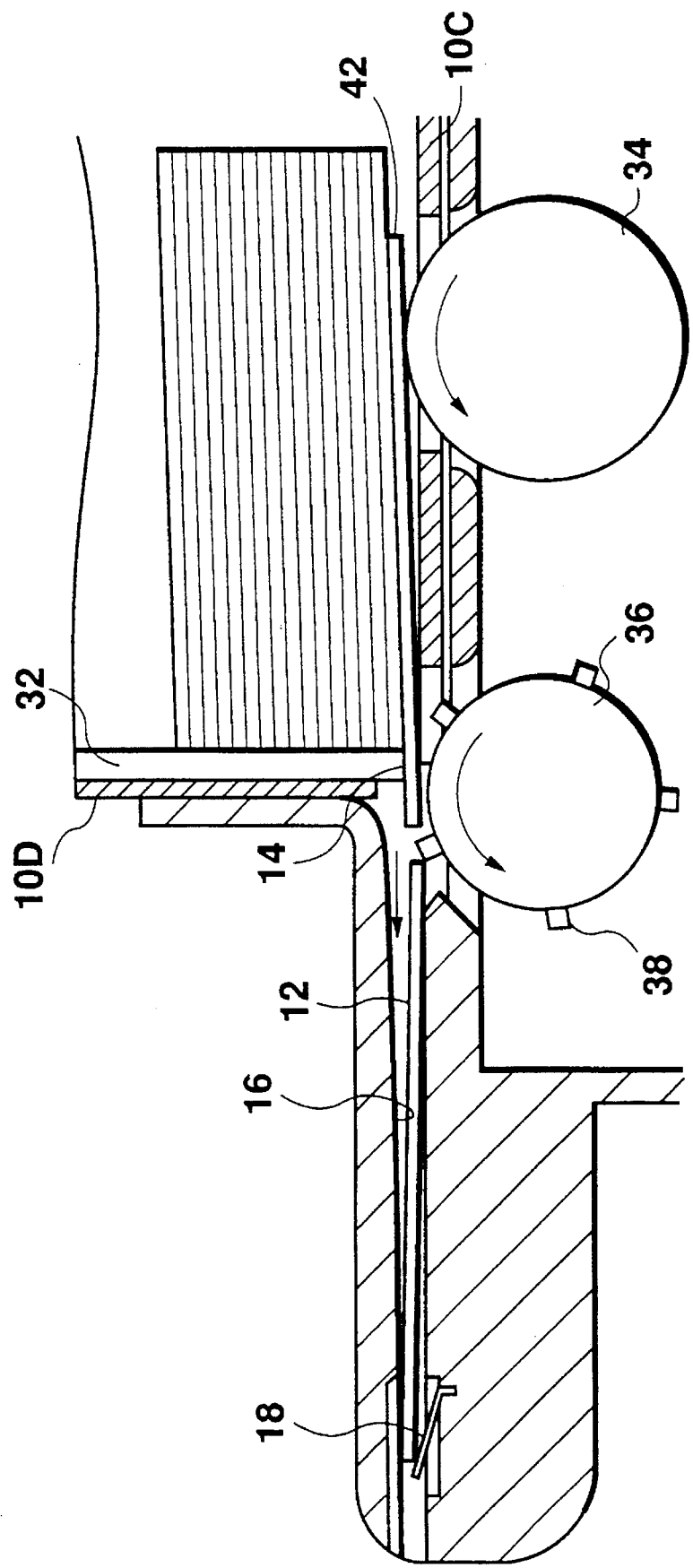
FIG. 6 shows the operation of the first embodiment.
Figure 7:
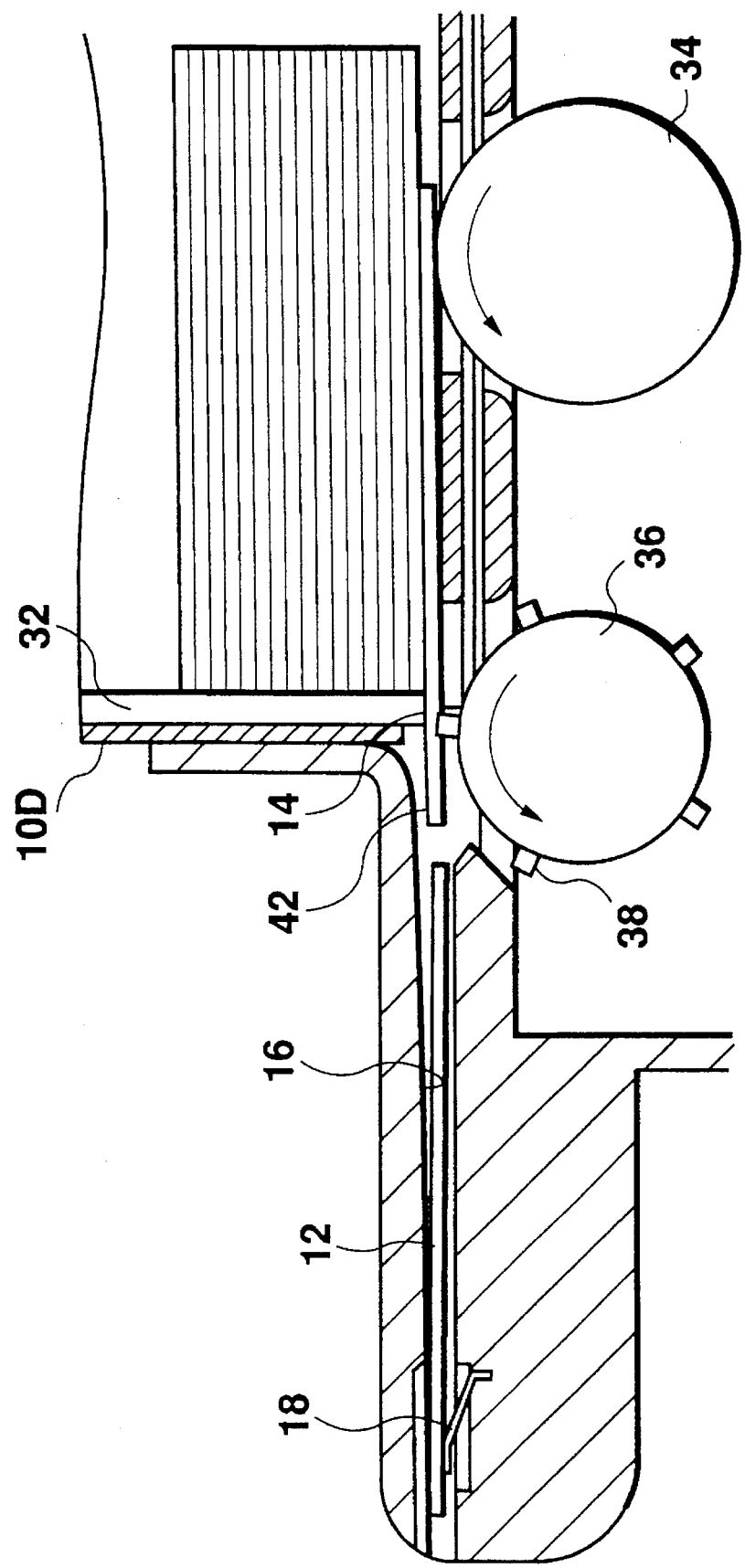
FIG. 7 shows the operation of the first embodiment.

As shown in FIG. 5, in the present embodiment, the distance from the ejection opening 14 to the proximal end of the plate spring type switch 18 approximately corresponds to the length of one glass sheet. Strictly speaking, this distance corresponds to the total of the length of one glass sheet and a certain margin inclusive of the width of the protrusion 38. In such a positional relationship, in the state where the glass sheet 12 falls in front of the upper protrusion 38, the leading edge of the glass sheet 12 is positioned at the proximal end of the switch 18, and as shown in FIG. 6, when the front roller 36 is rotated, the glass sheet 12 can be pushed by the protrusion to push down the switch 18 by the leading edge of the glass sheet 12. This state is shown in Figs. 6 and 7. Even if the returning force of the switch 18 is relatively strong, the pushing operation can be strongly carried out according to the apparatus of the present. embodiment, and therefore, it is possible to securely carry out activation of the switch 18.

Figure 8:
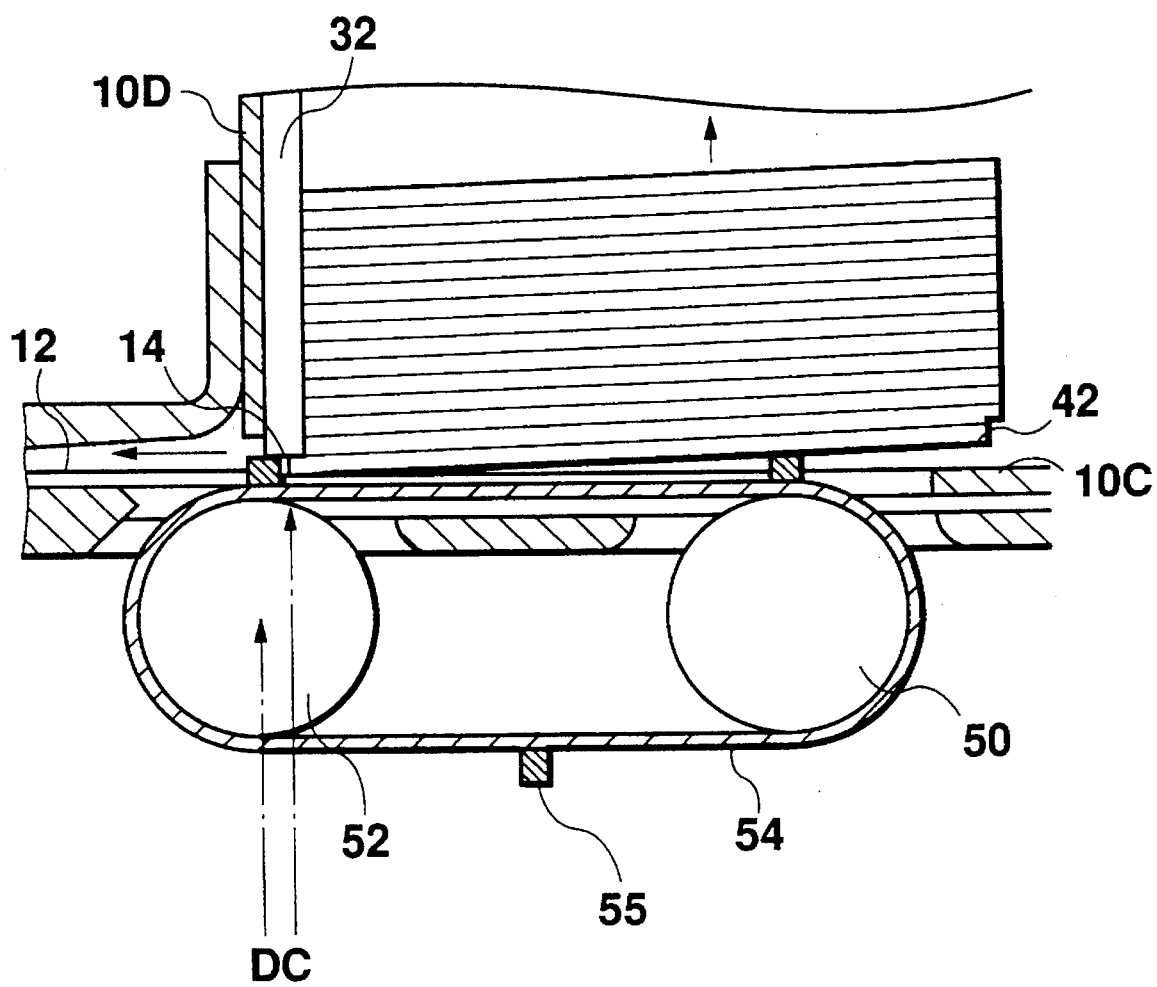
FIG. 8 is a sectional view illustrating a second embodiment of the apparatus for automatically delivering a glass sheet for a preparation according to the present invention.
Figure 9:
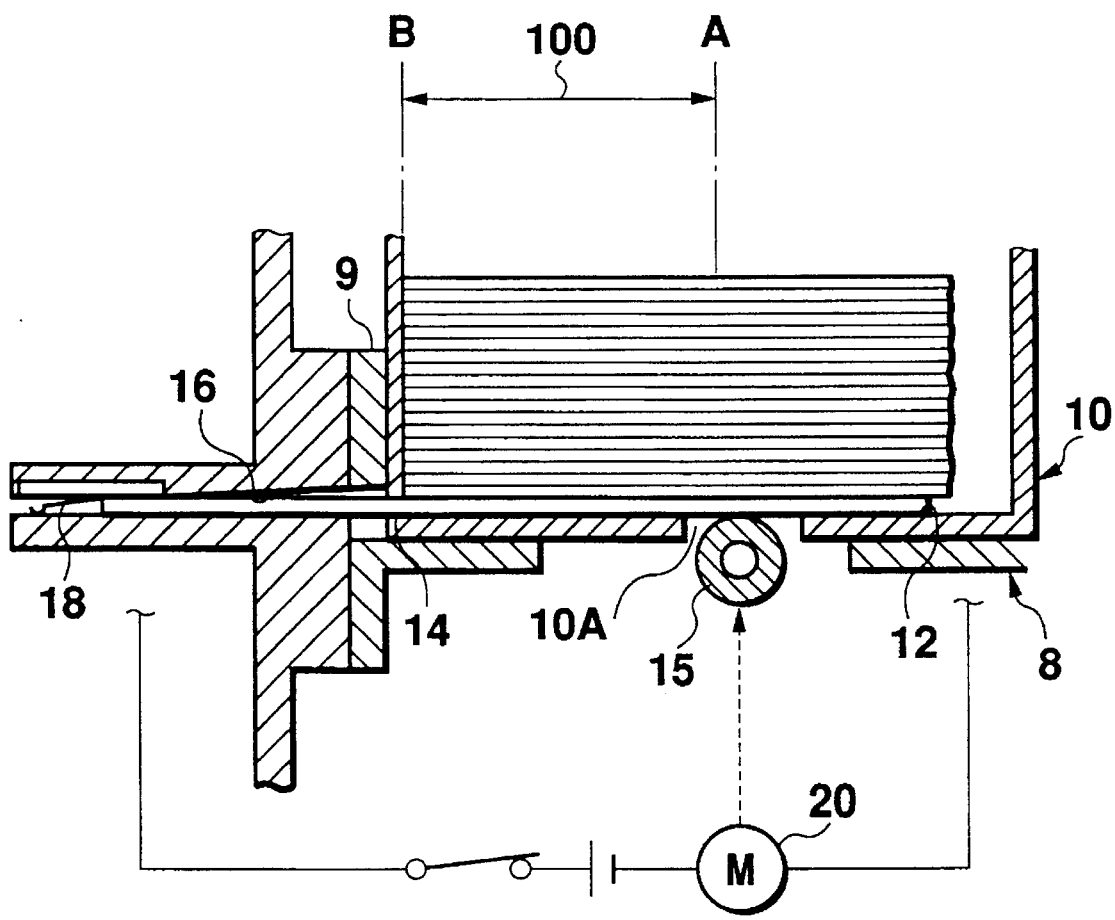
FIG. 9 shows a conventional apparatus.
Figure 10:
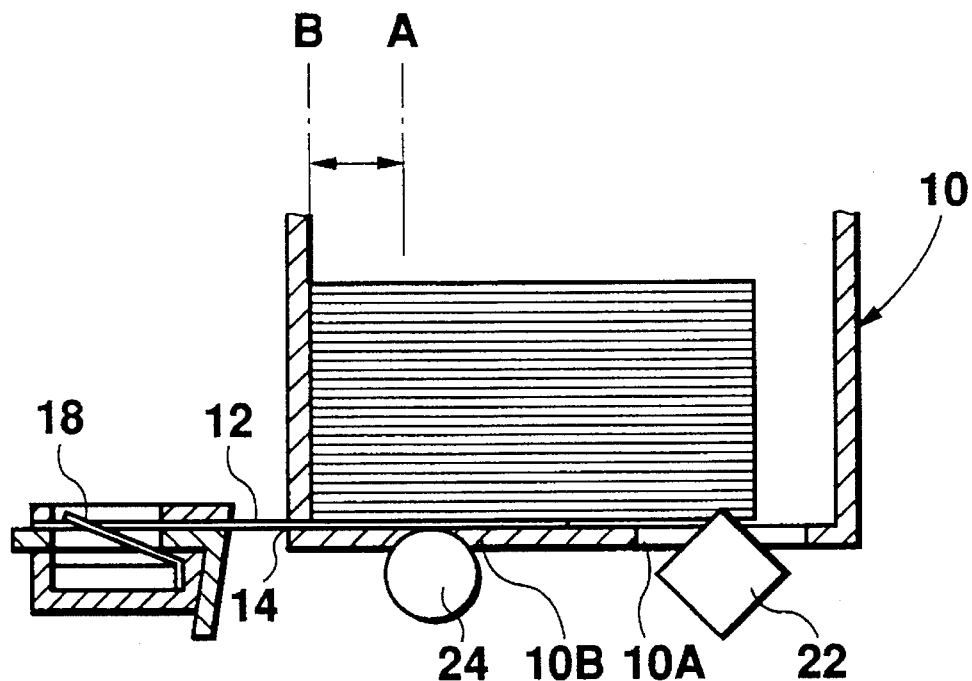
FIG. 10 shows another conventional apparatus.
Figure 11:
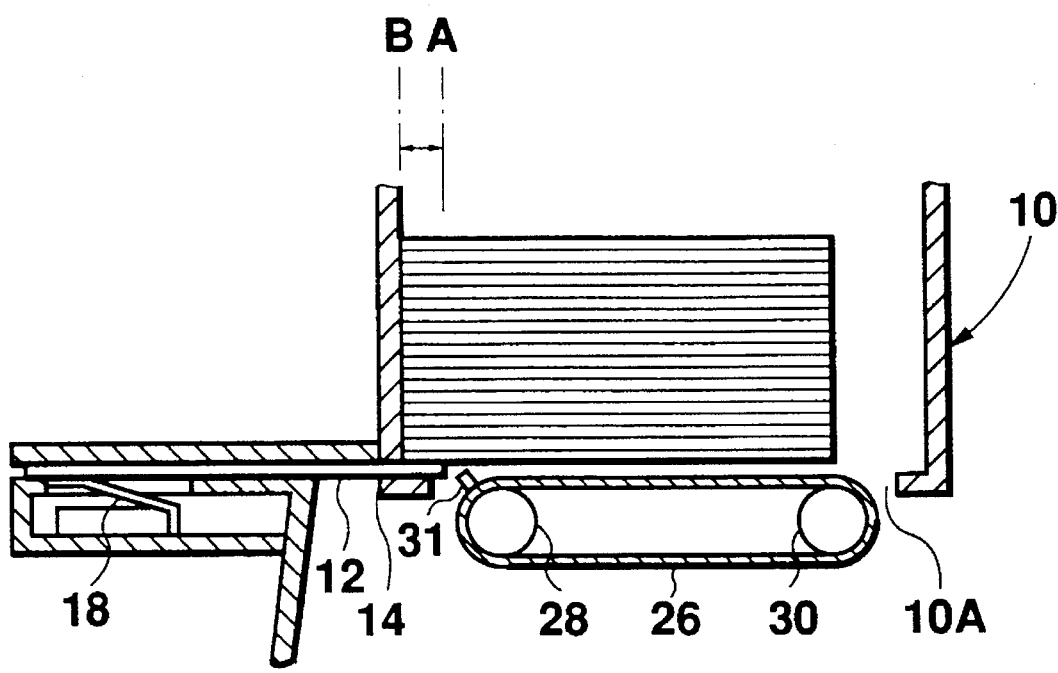
FIG. 11 shows still another conventional apparatus.

In FIG. 8, there is shown the second embodiment of the apparatus for automatically delivering glass sheets for prepared slides according to the present invention.

In the second embodiment, a belt 54 is passed over a rear roller 50 and a front roller 52, and the upper portion of the belt 54 protrudes into an opening formed in the bottom surface plate 10C and comes in contact with the lower surface of the lowest glass sheet 42. In this case, the position D of the axial center of the front roller is present substantially just under or in front of the position C of the ejection opening 14.

Here, the belt surface is formed with at least one protrusion 55. The protrusion 55 has a feeding function, a vibrating function and a pushing function for the glass sheets, as in the first embodiment described above. Fig. 8 shows a state where the glass sheet 12 is pushed, in which state the next glass sheet 42 is fed out by the next protrusion.

As shown in FIG. 8, in a state where the glass sheet 12 is ejected out of the ejection opening 14 by the movement of the belt 54, the glass sheet 12 no longer contacts with the belt 54. However, when the rear roller 50 and the front roller 52 are further rotated, the belt 54 moves forward, so that the protrusion 55 on the belt surface appears on its upper side. Then, the side of the protrusion 55 positioned on the upper side naturally hits against the trailing edge of the glass sheet 12 to push the glass sheet. A stroke distance of the glass sheet which can be pushed by the side of the protrusion 55 is decided by a relationship between the thickness of the ejected glass sheet 12 and the orbit of the protrusion 55, and it depends upon the diameter of the front roller 52.

An opening into which the belt 54 protrudes is formed approximately in the center of the bottom surface plate 10C.

In the first and second embodiments, it is desired that the front roller is set as close as possible to a position substantially just under the ejection opening 14, so long as a certain feed distance is obtained by the pushing. If the front roller is set in such a manner, the complete ejection of the glass sheet can be realized. In addition, the projection amount of the glass sheet projecting from the ejection opening 14, when the feeding is stopped, can be minimized, so that when the rack is obliquely raised from its rear portion to remove the same from the body, the projected portion of the glass sheet can be prevented from breaking.

As described above, according to the present invention, the glass sheet can be simply and easily pulled out and removed. Furthermore, the plate spring type switch for automatic feed stop can be securely pushed down by the leading edge of the glass sheet 12. Moreover, the roller with the protrusions or the belt with the protrusions can be utilized in a versatile manner to simplify construction.

What is claimed is:

1. An apparatus for automatically delivering a glass sheet for a preparation, comprising:

a rack having a surface for receiving a stack of glass sheets;

feed means for feeding out a lowest glass sheet in the stack until the lowest glass sheet has been completely ejected from the stack; and a switch mechanism operable to terminate operation of said feed means, said switch mechanism being operable by contact of a leading edge of the lowest glass sheet, wherein said feed means includes push means for pushing a trailing edge of the lowest glass sheet in order to operate said switch mechanism by said contact when the lowest glass sheet has been completely pushed out from the stack.

2. An apparatus for automatically delivering glass sheets for prepared slides, comprising:

a rack having a surface for receiving a stack of glass sheets for the prepared slides; and a body on which the rack is mounted and which successively delivers the lowest glass sheet, wherein said rack has an ejection opening which is formed in the lower end of a rack front surface plate to eject the lowest glass sheet individually, a rear opening formed in a rack bottom surface plate, and a front end opening formed in the rack bottom surface plate;

said body having a rear roller which protrudes into the rear opening and comes in contact with the lower surface of the lowest glass sheet to feed out said lowest glass sheet, and a front roller which has at least one protrusion on a roller surface which protrudes into the front end opening; and said protrusion of the roller surface coming into contact with the lower surface of the lowest glass sheet to feed it out and pushing the trailing edge of the ejected glass sheet in order to push down a delivery stop switch by the leading edge of the glass sheet ejected through the ejection opening.

3. The apparatus for automatically delivering glass sheets for prepared slides according to claim 2 wherein an axis of the front roller is positioned under or in front of a position of the ejection opening.

4. The apparatus for automatically delivering glass sheets for prepared slides according to claim 2 wherein a pushing stroke of the protrusion to the glass sheet is determined by a relationship between a thickness of the glass sheet, intended to be delivered by the apparatus, and the orbit of the protrusion.

5. The apparatus for automatically delivering glass sheets for prepared slides according to claim 2 wherein the size of the ejection opening is determined by the level of an aperture setting bar provided on said rack front surface plate with respect to said rack bottom surface plate.

6. The apparatus for automatically delivering glass sheets for prepared slides according to claim 2 wherein the rear opening and the front end opening are formed substantially at the center of the rack bottom surface plate.

7. The apparatus for automatically delivering glass sheets for prepared slides according to claim 2 wherein the roller surface of the rear roller has at least one protrusion.

8. An apparatus for automatically delivering a glass sheet for a preparation, comprising:

a receiving member for receiving leading edges of a stack of glass sheets;

a belt mechanism operable to move in a direction to urge the stack against the receiving member; and a switch mechanism operable to terminate operation of said belt mechanism by contact of a leading edge of a lowest glass sheet, wherein said belt mechanism includes a protrusion, during operation of the belt mechanism, capable of contacting a lower surface of the lowest glass sheet for pulling the lowest glass sheet out of the stack, which is prevented from moving forward by the receiving member, and for pushing a trailing edge of the lowest glass sheet in order to operate said switch mechanism by said contact when the lowest glass sheet has been completely pulled out of the stack.

9. The apparatus according to claim 8 wherein said belt mechanism includes a belt wound around a front roller, and an axis of the front roller is positioned under or in front of a position of the receiving member.

10. The apparatus according to claim 8 wherein a pushing stroke of the protrusion to the glass sheet is determined by a relationship between a thickness of the glass sheet, intended to be delivered by the apparatus, and the orbit of the protrusion.

11. The apparatus according to claim 8 wherein a level of said receiving member is defined for allowing glass sheets of different thickness to be separated from a stack of glass sheets.

12. The apparatus for automatically delivering glass sheets for prepared slides according to claim 8 wherein the opening is formed substantially at the center of the rack bottom surface plate.

* * * * *